United States Patent [19]

Hoehn

[11] 4,191,831
[45] Mar. 4, 1980

[54] IMIDAZOLYLETHOXY DERIVATIVES OF PYRIDIN-5-METHANOLS

[75] Inventor: Hans Hoehn, Tegernheim, Fed. Rep. of Germany

[73] Assignee: E. R. Squibb & Sons, Inc., Princeton, N.J.

[21] Appl. No.: 954,730

[22] Filed: Oct. 25, 1978

[51] Int. Cl.² ............................................ C07D 401/12
[52] U.S. Cl. .................................. 546/278; 424/263; 546/301; 546/303; 548/341
[58] Field of Search ................................ 546/278, 334

[56] References Cited

U.S. PATENT DOCUMENTS 2,580,475   1/1952   Sperber et al. ....................... 546/278

OTHER PUBLICATIONS

Heeres et al, J. Med. Chem. vol. 19, pp. 1148–1155 (1976).
Mostmans et al, J. Med. Chem. vol. 20, pp. 1511–1516 (1977).
Heeres et al, J. Med. Chem. vol. 20, pp. 1516–1520 (1977).

*Primary Examiner*—John D. Randolph
*Attorney, Agent, or Firm*—Lawrence S. Levinson; Dale Lovercheck

[57] ABSTRACT

Imidazolylethoxy derivatives of pyridin-5-methanols having the general formula

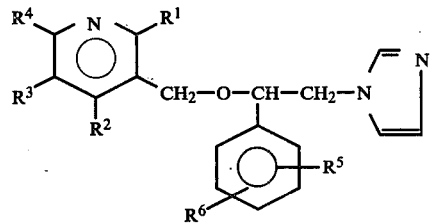

and their acid addition salts are useful as antifungal and antibacterial agents.

10 Claims, No Drawings

IMIDAZOLYLETHOXY DERIVATIVES OF PYRIDIN-5-METHANOLS

SUMMARY OF THE INVENTION

This invention relates to new 2-(1H-imidazol-1-yl)ethoxy derivatives of pyridin-5-methanols and the acid addition salts of these compounds. These new compounds have the general formula

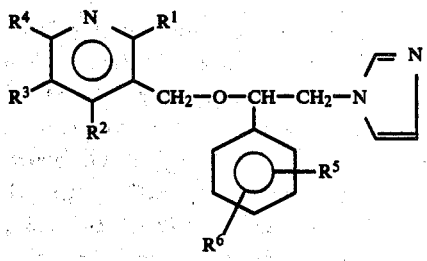

The symbols have the following meaning in Formula I and throughout the specification:

$R^1$ to $R^6$ each is hydrogen, hydroxy, halogen, lower alkoxy, lower alkylthio or lower alkyl.

DETAILED DESCRIPTION OF THE INVENTION

The lower alkyl groups include straight or branched chain hydrocarbon groups containing 1 to 7 carbon atoms. Examples include methyl, ethyl, propyl, isopropyl and the like. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$–$C_4$, especially $C_1$–$C_2$, lower alkyl groups are preferred.

The halogens are the four common halogens, chlorine and bromine being preferred in that order. Preferably, but not necessarily, all halogens in a single compound are the same.

Preferred embodiments of this invention are compounds of formula I wherein $R^1$ to $R^6$ each is hydrogen, lower alkyl of 1 to 4 carbons or halogen (especially chlorine or bromine).

Most preferred embodiments are compounds of formula I wherein $R^1$ to $R^6$ each is hydrogen, halogen or lower alkyl of 1 to 4 carbons, must especially wherein $R^1$ is hydrogen or $C_1$–$C_4$-alkyl, $R^2$, $R^4$, $R^5$ and $R^6$ each is chlorine, and $R^3$ is hydrogen.

The new compounds of formula I are formed by the following series of reactions.

A pyridine-5-carboxylic acid ester of the formula

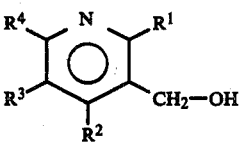

is reduced by means of a reducing agent, e.g., a metal hydride such as lithium aluminum hydride or sodium borohydride and the like, to give the alcohol of the formula

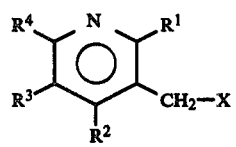

The alcohol of formula III is then converted to the halomethyl derivative of the formula

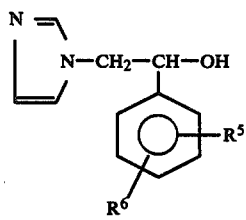

wherein X represents a halogen, preferably chlorine, bromine or iodine, by means of an inorganic acid halide such as thionyl chloride, phosphorus oxybromide, etc.

The product of formula I is then prepared by reaction of the halo compound of formula IV with a substituted 1-(phenyl)-2-(1H-imidazol-1-yl)ethanol of the formula The inorganic acid formed during the reaction is neutralized by a base, e.g., alkali metal hydoxide, carbonate, amine, alcoholate or other similar agents known in the art.

The compounds of formula II, which are used as starting materials, are produced by the procedures described in C.R. Acad. Sci. Hebd., Sci. Ser. C 275, 1317 (1972); Rec.trav.chim. 65, 129 (1946); Chem. Ber. 93, 1848 (1960). The compounds of formula V which are used as starting materials are produced by the general method described in J. Med. Chem. 12, 784 (1969).

The compounds of formula I form salts which are also part of this invention. The salts include acid-addition salts, particularly the non-toxic, physiologically acceptable members. The bases of formula I form salts by reaction with one or more equivalents of any of a variety of the common inorganic and organic acids providing acid addition salts including, for example, hydrohalides (especially hydrochloride and hydrobromide), sulfate, nitrate, borate, phosphate, oxalate, maleate, citrate, acetate, ascorbate, succinate, benzenesulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts may then be formed from the free base by reaction with one or more equivalents of acid containing the desired acid group.

The new compounds of Formula I and their salts are useful as anti-fungal and anti-bacterial agents and may be used to combat infections in various mammalian species, such as mice, rats, dogs, guinea pigs and the like, particularly those due to organisms such as *Candida albicans*, as well as organisms such as *Trichomonas vaginalis* or *Trichophyton mentagrophytes*. For example, a compound or mixture of compounds of formula I or physiologically acceptable acid addition salt thereof can be administered orally to an infected animal, e.g., to a mouse, in an amount of about 5 to 25 mg. per kg. per day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following examples are illustrative of the invention. Temperatures are on the Celsius scale.

EXAMPLE 1

2,4-Dichloro-5-[[1-(2,4-dichlorophenyl)-2-(1H-imidazol-1-yl)ethoxy]methyl]pyridine, hydrochloride (1:1)

(a) 2,4-Dichloropyridin-5-methanol 66 g. of 2,4-Dichloropyridin-5-carboxylic acid, ethyl ester (0.3 mol.) are dissolved in 120 ml. of anhydrous tetrahydrofuran. Nitrogen is passed through the flask and while stirring and cooling to 0°, 7.12 g. of lithium aluminum hydride are added in portions in order to keep the reaction temperature in the range of 5° to 10°. Stirring is continued for an additional 2 hours while cooling externally with ice water, and the mixture is allowed to stand overnight. While stirring and cooling the mixture with ice water, there are added 250 ml. of hydrochloric acid (3N) dropwise so that the reaction temperature does not exceed 5° to 8°. Then the acidic solution is evaporated in vacuo to dryness and the residual product is extracted with 500 ml. of chloroform. The chloroform extract is treated with charcoal, filtered and the solvent is distilled off, yielding 37.7 g. of 2,4-dichloropyridin-5-methanol, m.p. 73°–77°.

The salt product, which is the residue after extracting with chloroform is neutralized with sodium hydroxide and the salt mixture is again extracted with chloroform in a Soxhlet apparatus and this yields a second crop of 5.2 g. Total yield 42.9 g. (80%). After recrystallization from hexane, the 2,4-dichloropyridin-5-methaol melts at 82°–85°.

(b) 5-Chloromethyl-2,4-dichloropyridine 20.2 g. of 2,4-dichloropyridin-5-methanol (0.11 mol.) and 150 ml. of phosphorus oxychloride are refluxed for 19 hours. Then the excess phosphorus oxychloride is removed in vacuo and ice is added to the residue. 5-Chloromethyl-2,4-dichloropyridine is filtered off, washed with water, dried in the desiccator over $P_2O_5$ and recrystallized from hexane; yield 17.95 g. (83%), m.p. 55°–56°.

(c)

2,4-Dichloro-5-[[1-(2,4-dichlorophenyl)-2-(1H-imidazoyl-1-yl)ethoxy]methyl]pyridine, hydrochloride (1:1)

In a three-necked flask, fitted with stirrer, reflux condenser and gas inlet tube 29.3 g. of sodium hydroxide (0.73 mol.) and 27 ml. of water are introduced. While passing nitrogen through the flask, the solution is cooled to 45° and then 7.71 g. of 1-(2,4-dichlorophenyl)-2-(1H-imidazol-1-yl)ethanol (0.03 mol.) [prepared by the method of J. Med. Chem. 12, 784 (1969)], 0.5 g. of benzyltrimethylammonium chloride and 30 ml. of tetrahydrofuran are added. To the mixture, which is warmed to 50°, 5.9 g. of 5-chloromethyl-2,4-dichloropyridine are added and the mixture is stirred vigorously for two hours at 60°. The filtered biphasic solution is transferred into a separating funnel, the lower aqueous sodium hydroxide is extracted with 10 ml. of tetrahydrofuran. The combined tetrahydrofuran layers are treated with charcoal and dried by means of sodium sulfate. Ether is then added to the tetrahydrofuran extract in order to remove an oily by-product. To the clear solution of the free base alcoholic hydrochloric acid is added dropwise. The precipitated 2,4-dichloro-5-[[1-(2,4-dichlorophenyl)-2-(1H-imidazol-1-yl)-ethoxy]-methyl]pyridine, hydrochloride (3.5 g.) is treated with acetonitrile. A second crop is obtained by removing the tetrahydrofuran/alcohol mother liquor and treating the residue with acetonitrile (3.5 g.), m.p. 177°. Total yield 7 g. (52%). Recrystallization from acetonitrile elevates the melting point to 181°–182°.

EXAMPLE 2

2,4-Dichloro-6-methyl-5-[[1-(2,4-dichlorophenyl)-2-(1H-imidazol-1-yl)ethoxy]methyl]pyridine, hydrochloride By substituting 0.3 ml. of 2,4-dichloro-6-methylpyridin-5-carboxylic acid, ethyl ester for the 2,4-dichloropyridin-5-carboxylic acid, ethyl ester in the procedure of Example 1, 2,4-dichloro-6-methyl-5-[[1-(2,4-dichlorophenyl)-2-(1H-imidazol-1-yl)-ethoxy]methyl]pyridine and its hydrochloride, m.p. 225°–260° are obtained, nitrate m.p. 121°–122°.

The following additional products of formula C are obtained by the procedure of Example 1 by reacting the unsubstituted or substituted 1-phenyl-2-(1H-imidazol-1-yl)ethanol of formula A with the unsubstituted or substituted 5-chloromethylpyridine of formula B. The substituents apply to the respective formulas.

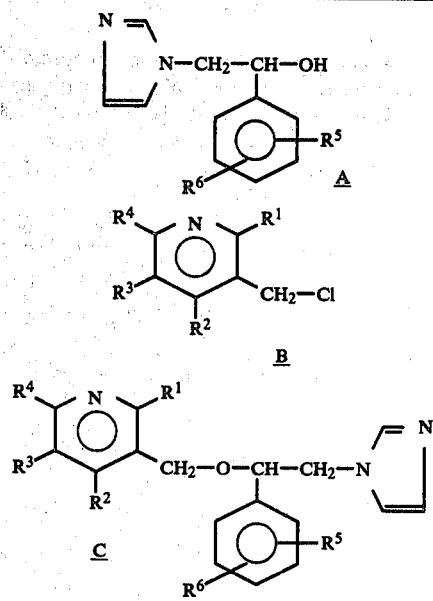

| Example | R¹ | R² | R³ | R⁴ | R⁵ | R⁶ |
|---|---|---|---|---|---|---|
| 3 | H | H | H | H | H | H |
| 4 | CH₃ | CH₃ | —OH | Cl | H | H |
| 5 | H | H | —OCH₂H₅ | —CH₃ | 2-Cl | 4-Cl |
| 6 | C₂H₅ | C₂H₅ | —OCH₃ | —CH₃ | H | 4-Cl |
| 7 | C₂H₅ | CH₃ | Br | H | H | 3-Br |
| 8 | H | CH₃ | H | H | 2-Br | 4-Br |
| 9 | C₂H₅ | H | Br | H | 3-Br | 4-Br |
| 10 | C₂H₅ | H | H | CH₃ | H | 4-Cl |
| 11 | C₂H₅ | H | Cl | C₂H₅ | H | 2-Cl |
| 12 | H | CH₃ | —OC₂H₅ | H | 2-CH₃ | 4-CH₃ |
| 13 | C₂H₅ | C₃H₇ | Cl | H | H | 4-OCH₃ |
| 14 | C₂H₅ | H | Cl | H | H | 2-OCH₃ |
| 15 | C₃H₇ | H | —OH | H | H | 3-Cl |
| 16 | Cl | H | Cl | H | 2-Cl | 4-Cl |
| 17 | Br | CH₃ | H | H | H | 4-Cl |
| 18 | —OCH₃ | H | Cl | H | H | H |
| 19 | —SCH₃ | H | Cl | H | 2-Cl | 4-Cl |
| 20 | OC₂H₅ | CH₃ | Cl | H | 3-Cl | 4-Cl |
| 21 | C₂H₅ | H | Cl | Cl | H | 4-Cl |
| 22 | C₂H₅ | —SCH₃ | H | H | 2-Cl | 4-Cl |
| 23 | C₂H₅ | CH₃ | Cl | H | H | 4-Cl |
| 24 | H | CH₃ | Br | H | H | 4-Cl |
| 25 | H | —OCH₃ | H | H | H | 4-Cl |
| 26 | C₂H₅ | H | Cl | H | 2-Cl | 4-Cl |
| 27 | C₂H₅ | H | H | CH₃ | H | 4-Br |
| 28 | H | H | Cl | H | 2-Cl | 4-Cl |
| 29 | OH | CH₃ | Cl | H | H | 4-Cl |
| 30 | CH₃ | H | —SCH₃ | H | H | 4-SCH₃ |
| 31 | C₂H₅ | H | H | H | H | 4-Cl |
| 32 | C₂H₅ | H | H | H | H | 4-C₂H₅ |
| 33 | H | —OH | H | H | 3-Cl | H |
| 34 | C₂H₅ | CH₃ | H | —OH | H | H |
| 35 | C₂H₅ | H | —OH | H | 2-Cl | 4-Cl |
| 36 | H | H | H | H | 4-OCH₃ | H |
| 37 | Cl | H | H | H | H | 2-SCH₃ |
| 38 | H | Br | H | Br | 4-SCH₃ | H |
| 39 | H | H | —OH | H | 3-OH | 5-OH |
| 40 | C₂H₅ | CH₃ | —OC₄H₉ | H | H | 4-Cl |
| 41 | H | H | —OC₃H₇ | H | 2-Cl | 4-Cl |
| 42 | H | H | H | —SCH₃ | 2-Cl | 4-Cl |
| 43 | Cl | H | Cl | —CH₃ | H | 4-Cl |

What is claimed is:
1. A compound of the formula

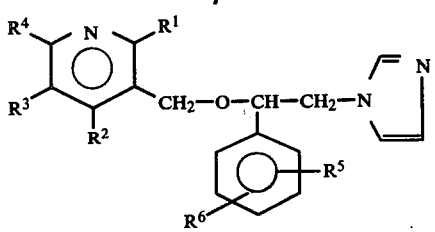

wherein
R¹ to R⁶ each is hydrogen, lower alkyl, lower alkoxy, lower alkylthio, hydroxy or halogen;
and acid addition salts thereof.

2. A compound as in claim 1 wherein R² and R⁴ each is halogen.

3. A compound as in claim 1 wherein R⁵ and R⁶ each is halogen.

4. A compound as in claim 2 wherein each halogen is chlorine.

5. A compound as in claim 3 wherein each halogen is chlorine.

6. A compound as in claim 1 wherein R¹ to R⁶ each is hydrogen, lower alkyl of 1 to 4 carbons or halogen.

7. A compound as in claim 1 wherein R¹ and R³ each is hydrogen; R² and R⁴ each is halogen; R⁵ is 2-halo; and R⁶ is 4-halo; and physiologically acceptable acid addition salts thereof.

8. A compound as in claim 1 wherein R¹ and R³ each is hydrogen; R² and R⁴ each is chloro; R⁵ is 2-chloro and R⁶ is 4-chloro.

9. A compound as in claim 1 wherein R¹ is methyl; R² and R⁴ is chloro; R³ is hydrogen; R⁵ is 2-chloro; R⁶ is 4-chloro; and acid addition salts thereof.

10. The hydrochloride of the compound of claim 8.

* * * * *

UNITED STATES PATENT AND TRADEMARK OFFICE
CERTIFICATE OF CORRECTION

PATENT NO. : 4,191,831
DATED : March 4, 1980
INVENTOR(S) : Hans Hoehn

It is certified that error appears in the above-identified patent and that said Letters Patent are hereby corrected as shown below:

Column 1, line 51, change "must" to -- most --.

Signed and Sealed this

Twenty-fourth Day of June 1980

[SEAL]

Attest:

SIDNEY A. DIAMOND

Attesting Officer    Commissioner of Patents and Trademarks